United States Patent
Pois et al.

(10) Patent No.: US 9,594,035 B2
(45) Date of Patent: Mar. 14, 2017

(54) SILICON GERMANIUM THICKNESS AND COMPOSITION DETERMINATION USING COMBINED XPS AND XRF TECHNOLOGIES

(71) Applicants: Heath A. Pois, Fremont, CA (US); Wei Ti Lee, San Jose, CA (US)

(72) Inventors: Heath A. Pois, Fremont, CA (US); Wei Ti Lee, San Jose, CA (US)

(73) Assignee: ReVera, Incorporated, Santa Clara, CA (US)

(*) Notice: Subject to any disclaimer, the term of this patent is extended or adjusted under 35 U.S.C. 154(b) by 0 days.

(21) Appl. No.: 14/691,164

(22) Filed: Apr. 20, 2015

(65) Prior Publication Data
US 2015/0308969 A1    Oct. 29, 2015

Related U.S. Application Data

(60) Provisional application No. 61/984,286, filed on Apr. 25, 2014.

(51) Int. Cl.
*G01N 23/22* (2006.01)
*G01B 15/02* (2006.01)
(Continued)

(52) U.S. Cl.
CPC ......... *G01N 23/2208* (2013.01); *G01B 15/02* (2013.01); *G01N 23/223* (2013.01);
(Continued)

(58) Field of Classification Search
CPC .............. G01N 23/2208; G01N 23/223; G01N 23/2273; G01N 2233/61; G01N 2233/6116; G01B 15/02; G01B 15/025
See application file for complete search history.

(56) References Cited

U.S. PATENT DOCUMENTS

| 7,358,494 | B1 |   | 4/2008 | Gao et al. |
| 8,513,603 | B1 | * | 8/2013 | Lederman ............ G01N 23/223 250/305 |

(Continued)

FOREIGN PATENT DOCUMENTS

KR    10-1241007    3/2013

OTHER PUBLICATIONS

Andrieu et al, "SiGe Channel p-MOSFETs Scaling-Down", 33rd Conference of European Solid-State Device Research.*

(Continued)

*Primary Examiner* — David E Smith
(74) *Attorney, Agent, or Firm* — Blakely Sokoloff Taylor Zafman LLP

(57) ABSTRACT

Systems and approaches for silicon germanium thickness and composition determination using combined XPS and XRF technologies are described. In an example, a method for characterizing a silicon germanium film includes generating an X-ray beam. A sample is positioned in a pathway of said X-ray beam. An X-ray photoelectron spectroscopy (XPS) signal generated by bombarding said sample with said X-ray beam is collected. An X-ray fluorescence (XRF) signal generated by bombarding said sample with said X-ray beam is also collected. Thickness or composition, or both, of the silicon germanium film is determined from the XRF signal or the XPS signal, or both.

10 Claims, 12 Drawing Sheets

(51) Int. Cl.
*G01N 23/223* (2006.01)
*G01N 23/227* (2006.01)

(52) U.S. Cl.
CPC ..... *G01N 23/2273* (2013.01); *G01N 2223/61* (2013.01); *G01N 2223/6116* (2013.01)

(56) References Cited

U.S. PATENT DOCUMENTS

| | | | |
|---|---|---|---|
| 2006/0062350 A1* | 3/2006 | Yokhin | G01N 23/20008 378/86 |
| 2008/0159474 A1 | 7/2008 | Hubbard-Nelson et al. | |
| 2012/0045855 A1 | 2/2012 | Beck et al. | |
| 2013/0077742 A1* | 3/2013 | Schueler | G21K 1/06 378/44 |
| 2015/0032398 A1* | 1/2015 | Peterlinz | G01N 23/2206 702/81 |

OTHER PUBLICATIONS

International Search Report and Written Opinion from PCT/US2015/026935 mailed Aug. 26, 2015, 15 pgs.

Andrieu, F. et al., "SiGe Channel p-MOSFETs Scaling-Down" European Solid-State Device Research, 2003 33rd Conference on. ESSDERC '03, 5 pgs.

Cheng, K. et al., "High Performance Extremely Thin SOI (ETSOI) Hybrid CMOS with Si Channel NFET and Strained SiGe Channel PFET," IEEE (2012) 4 pgs.

Liu, Q. et al., "High Performance UTBB FDSOI Devices Featuring 20nm Gate Length for 14nm Node and Beyond," IEEE (2013) 4 pgs.

Ghani, T. et al., "A 90nm High Volume Manufacturing Logic Technology Featuring Novel 45nm Gate Length Strained Silicon CMOS Transistors", 2003 IEEE, IEDM. Technical Digest, pp. 978-980, 3 pgs.

International Preliminary Report on Patentability from PCT/US2015/026935 mailed Nov. 3, 2016, 12 pgs.

* cited by examiner $$I_{Ge} = \frac{f}{K_{Ge}} A(t, \lambda) \qquad (1)$$

$$I_{Si} = \frac{(1-f)}{K_{Si}} A(t, \lambda) \qquad (2)$$

$$I_{GeL\alpha} = \frac{f}{K_{GeL\alpha}} A(t, \lambda) \qquad (3)$$

$$I_{Ge} = \frac{f}{K_{Ge}} \left(1 - e^{-t/(f\lambda_{cGe}(Ge) + (1-f)\lambda_{cSi}(Ge))}\right) \quad (1)$$

$$I_{Si} = (1-f)\left(1 - e^{-t/(f\lambda_{cGe}(Si) + (1-f)\lambda_{cSi}(Si))}\right) \\ + e^{-t/(f\lambda_{cGe}(Si) + (1-f)\lambda_{cSi}(Si))} \quad (2)$$

$$I_{GeLa} = \frac{f}{K_{GeLa}} \left(1 - e^{-t/(f\lambda_{cGe}(GeLa) + (1-f)\lambda_{cSi}(GeLa))}\right) \quad (3)$$

SUMMARY OF MEASUREMENT PRECISION

| Precision (% RSD of mean value) of XPS-XRF measurements on UTBB FDSOI product wafers in 50μm2 metrology box | | |
|---|---|---|
| | *SiGe Thickness* | *Ge %AC* |
| Static precision (30x 2-sites) | 0.69% | 0.63% |
| Dynamic precision (18x 5-sites) | 0.70% | 0.65% |
| Long term stability (>4 months) | 0.53% | 0.33% |

FIG. 9

SILICON GERMANIUM THICKNESS AND COMPOSITION DETERMINATION USING COMBINED XPS AND XRF TECHNOLOGIES

CROSS-REFERENCE TO RELATED APPLICATIONS

This application claims the benefit of U.S. Provisional Application No. 61/984,286, filed on Apr. 25, 2014, the entire contents of which are hereby incorporated by reference herein.

BACKGROUND

1) Field

Embodiments of the invention are in the field of combined XPS and XRF technologies and, in particular, silicon germanium thickness and composition determination using combined XPS and XRF technologies.

2) Description of Related Art

X-ray photoelectron spectroscopy (XPS) is a quantitative spectroscopic technique that measures the elemental composition, empirical formula, chemical state and electronic state of the elements that exist within a material. XPS spectra may be obtained by irradiating a material with a beam of X-rays while simultaneously measuring the kinetic energy and number of electrons that escape from the top, e.g., 1 to 10 nm of the material being analyzed. XPS analysis commonly employs monochromatic aluminum Kα (AlKα) X-rays, which may be generated by bombarding an aluminum anode surface with a focused electron beam. A fraction of the generated AlKα X-rays is then intercepted by a focusing monochromator and a narrow X-ray energy band is focused onto the analysis site on a sample surface. The X-ray flux of the AlKα X-rays at the sample surface depends on the electron beam current, the thickness and integrity of the aluminum anode surface, and crystal quality, size, and stability of the monochromator.

X-ray fluorescence (XRF) is the emission of characteristic "secondary" (or fluorescent) X-rays from a material that has been excited by bombarding with higher energy X-rays or gamma rays. The phenomenon is widely used for elemental analysis and chemical analysis, particularly in the investigation of metals, glass, ceramics and building materials, and for research in geochemistry, forensic science and archaeology.

XPS analysis and XRF analysis each have their own advantages as techniques for sample characterization. Thus, advances are needed in analyses based on XPS and/or XRF detection.

SUMMARY

One or more embodiments are directed to silicon germanium thickness and composition determination using combined XPS and XRF technologies.

In an embodiment, a method for characterizing a silicon germanium film includes generating an X-ray beam. A sample is positioned in a pathway of said X-ray beam. An X-ray photoelectron spectroscopy (XPS) signal generated by bombarding said sample with said X-ray beam is collected. An X-ray fluorescence (XRF) signal generated by bombarding said sample with said X-ray beam is also collected. Thickness of the silicon germanium film is determined from the XRF signal and the XPS signal.

In another embodiment, a method for characterizing a silicon germanium film includes generating an X-ray beam. A sample is positioned in a pathway of said X-ray beam. An X-ray photoelectron spectroscopy (XPS) signal generated by bombarding said sample with said X-ray beam is collected. An X-ray fluorescence (XRF) signal generated by bombarding said sample with said X-ray beam is also collected. Composition of the silicon germanium film is determined from the XRF signal and the XPS signal.

In another embodiment, a system for characterizing a silicon germanium film includes an X-ray source for generating an X-ray beam. The system also includes a sample holder for positioning a sample in a pathway of said X-ray beam. The system also includes a first detector for collecting an X-ray photoelectron spectroscopy (XPS) signal generated by bombarding said sample with said X-ray beam. The system also includes a second detector for collecting an X-ray fluorescence (XRF) signal generated by bombarding said sample with said X-ray beam. The XRF signal or the XPS signal, or both, are for determining a thickness or a composition, or both, of the silicon germanium film.

BRIEF DESCRIPTION OF THE DRAWINGS

FIG. 3B includes elaborated equations (1)-(3) of FIG. 3A that describe the relationships between each of the intensities and the thickness of a SiGe film, in accordance with an embodiment of the present invention.

FIG. 9 includes a table showing a summary of measurement precision, in accordance with an embodiment of the present invention.

DETAILED DESCRIPTION

Figure 1:
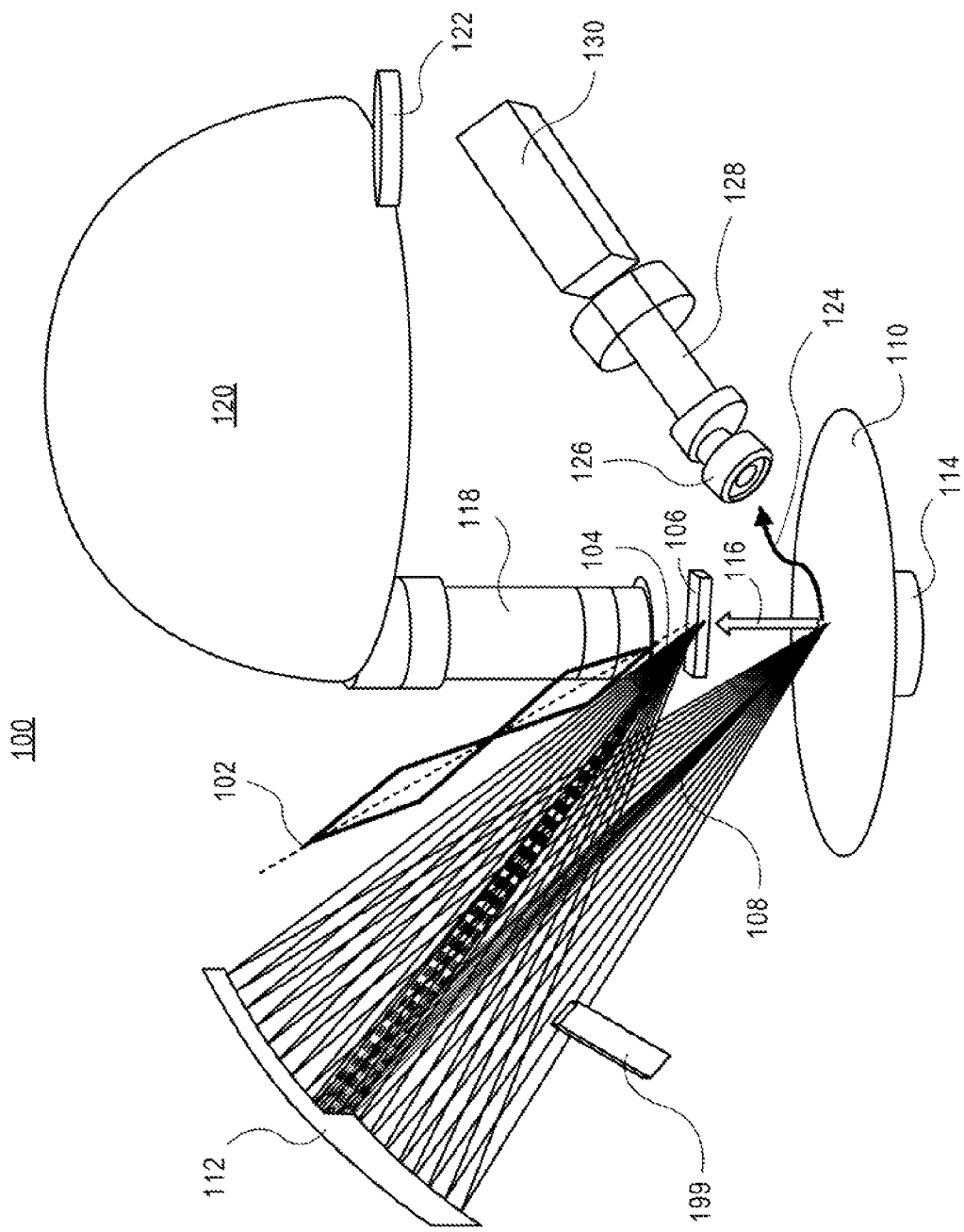
FIG. 1 illustrates an angled view of an XPS and XRF combination tool, in accordance with an embodiment of the present invention.

One or more embodiments are directed to the detection and use of photoelectron and X-ray fluorescent signals from the silicon (Si) and germanium (Ge) atoms in a silicon germanium (SiGe) thin film in combination with a realistic material mixing model to allow for the unique, unambiguous and stable determination of the SiGe thickness and the Ge % atomic composition applicable to realistic fab production needs. In the following description, numerous specific details are set forth in order to provide a thorough understanding of embodiments of the present invention. It will be apparent to one skilled in the art that embodiments of the present invention may be practiced without these specific details. In other instances, well-known features such as entire semiconductor device stacks are not described in detail in order to not unnecessarily obscure embodiments of the present invention. Furthermore, it is to be understood that the various embodiments shown in the figures are illustrative representations and are not necessarily drawn to scale.

Embodiments of the present invention address the problem of simultaneous determination and process control of Silicon Germanium thickness and Ge % atomic composition. Technical advantages of embodiments of the present invention include providing new capability for accurate, repeatable determination of thin SiGe thickness and Ge % composition in a fab environment for production use.

More generally, one or more embodiments of the present invention employ the combination of XPS and XRF signals along with a realistic film stack model to simultaneously determine a thin film SiGe thickness and compositional film properties. New film-stack algorithms can be employed to most accurately and robustly determine the SiGe thickness and Ge composition (%) over significant ranges using both the XPS (Si, Ge3d) and XRF (GeL$\alpha$) measured intensities. In an exemplary embodiment, in order to properly represent the real compositional variation of the Si and Ge species in the SiGe layer, (i) a generic film stack model that accounts for the generation of a Si XPS signal from both the SiGe film and crystalline silicon substrate (if appropriate) is used, along with (ii) a realistic material layer mixing model that scales the predicted intensity of the XPS and XRF Ge signals relative to an otherwise pure Ge film, constraining the remaining fraction of the film to Si.

To provide context, over the past decade, SiGe technology has played an increasing role in p-type field effect transistor (pFET) performance boost and threshold voltage ($V_t$) tunability. Notably, SiGe embedded (e-SiGe) in the source-drain region produces uniaxial strain in p-type metal oxide semiconductor (PMOS) channels. More recently, SiGe is being considered as a replacement for the conventional Si channel to achieve higher hole mobility. Hence, thickness and composition of SiGe, especially channel SiGe (cSiGe) has become one of the critical control parameters for semiconductor device performance. Capability of in-line metrology directly on product wafers is highly desirable in high-volume manufacturing.

Existing optical metrology does not directly measure composition and requires reference metrology to validate a model which usually works only over a tight range of concentration and thickness. X-ray diffraction (XRD) is another commonly used technique for SiGe film measurements. However, XRD suffers from relaxation induced uncertainties, poor precision on films having a thickness less than 100 Angstroms, and slow measurement speed. Such drawbacks present challenges for current XRD solutions, especially in a high volume manufacturing process control in the product context. In accordance with one or more embodiments herein, measurements of both composition and thickness of a thin SiGe film on various substrates such as bulk-Si, silicon-on-insulator (SOI), and ultra-thin SOI, are achieved with simultaneous XPS and XRF measurements.

Providing further context, XPS has recently proven to be an effective metrology for ultrathin films (e.g., less than approximately 100 Angstroms in thickness), with good sensitivity to both composition and thickness. In particular, it is the metrology of choice for various high-k metal gate (HKMG) films in 32 nm, 28 nm and 20 nm device manufacturing as well as 16/14 nm Fin field effect transistor (FinFET) process development. However, for the case of thin cSiGe films on Si (or Si-containing) substrates, XPS cannot differentiate between the Si signal from the SiGe film and the signal from the Si substrate. With only one independent signal which is the Ge XPS signal, XPS alone cannot independently determine both variables, which are the composition and thickness. In accordance with one or more embodiments described herein, this problem is resolved by taking advantage of the GeL$\alpha$ XRF signal that is also generated at the same time during the XPS measurement. The XRF signal provides an additional independent signal that, when combined with the XPS signals, allows for the measurement of both thickness and composition.

In an aspect, both XPS and XRF information may be obtained from a single metrology tool. In an example, FIG. 1 illustrates an angled view of an XPS and XRF combination tool 100, in accordance with an embodiment of the present invention. Measurements described herein were performed on an in-line XPS and XRF combination tool such as combination tool 100. In one embodiment, the XPS and XRF combination tool 100 is capable of measuring 300 mm wafers within a 50 $\mu m^2$ metrology box.

Referring to FIG. 1, the XPS and XRF combination tool 100 is operated while maintained under a base pressure of less than approximately 1.0E-7 Torr. Using a LaB$_6$ electron gun 102 at a nominal beam current of approximately 600 $\mu A$, x-ray 104 is generated from an aluminum anode 106 at 1486.7 eV. A monochromatic AlK$\alpha$ x-ray 108 is then focused on to a wafer 110 by a high quality quartz crystal monochromator 112. A magnetic lens 114 under the wafer 110 generates magnetic field near the wafer 110 surface and focuses the photoelectrons 116 generated into an XPS spectrometer including XPS input optics 118, an XPS energy analyzer 120 (e.g., a Spherical Capacitor Analyzer (SCA)), and an XPS detector 122. The XPS spectrometer electron optics 118 directs and shapes the photoelectron beam 116 for best transmission into the XPS energy analyzer 120. The XPS energy analyzer 120 operates at fixed voltage difference between the spheres, and a pass energy of 141.2 eV is typically used.

Referring again to FIG. 1, simultaneously, the monochromatic AlK$\alpha$ x-ray 108 excites low energy x-ray fluorescence (LE-XRF) 124 from the wafer 110. The LE-XRF 124 is detected by using a Silicon Drift Detector (SDD) 126 located near the analysis point, approximately 1 mm above the wafer 110 surface. In one embodiment, the SDD detector 126 is cooled by dual Peltier coolers, and the operating temperature is maintained at approximately −30° C. To filter out stray electrons and UV light, an ultrathin aluminum window may be used at the SDD 126 entrance. SDD 126 is coupled to an XRF detector assembly 128. The XRF detector assembly 128 is coupled to SDD electronics 130.

The XPS and XRF combination tool 100 may also include a post-monochromator flux detector 199, as is depicted in FIG. 1. Although not depicted, XPS and XRF combination tool 100 may also be equipped with vision cameras. For example, a wafer-XY camera can be included for feature finding and pattern recognition on the wafer. A wafer-Z camera can be included for determining the wafer z-height for optimal x-ray spot focusing and positioning. An anode camera can be included that monitors the anode for optimal e-beam focus. Data acquisition may be integrated to the system software where both XPS and XRF signals are collected at the same time. In one such embodiment, total acquisition time is approximately 24 s per site.

In another aspect, analysis and algorithm development considerations are addressed. For example, in an embodiment, to ensure consistent measurements, ratios of XPS signals are used in the data analysis to eliminate variation from the x-ray source. Typically, an Si signal is used as the reference for most of the XPS data analysis. In the case for an XRF signal, the XRF signal is normalized with respect to the incoming x-ray flux for stable measurement. In one such embodiment, normalization with respect to the incoming x-ray flux is achieved by monitoring the post monochromator x-ray flux (e.g., at post-monochromator flux detector 199) in real-time during data acquisition.

In an embodiment, new film-stack algorithms were employed to most accurately and robustly determine the SiGe thickness and Ge composition (%) over significant ranges using both the XPS (Si, Ge3d) and XRF (GeLα) measured intensities. In a specific embodiment, in order to properly represent the real compositional variation of the Si and Ge species in the SiGe layer, (a) a generic film stack model that accounts for the generation of Si XPS signal from both the SiGe film and crystalline silicon substrate (if appropriate) is required, along with (b) a realistic material layer mixing model that scales the predicted intensity of the XPS and XRF Ge signals relative to an otherwise pure Ge film, constraining the remaining fraction of the film to Si.

Figures 2, 3A:
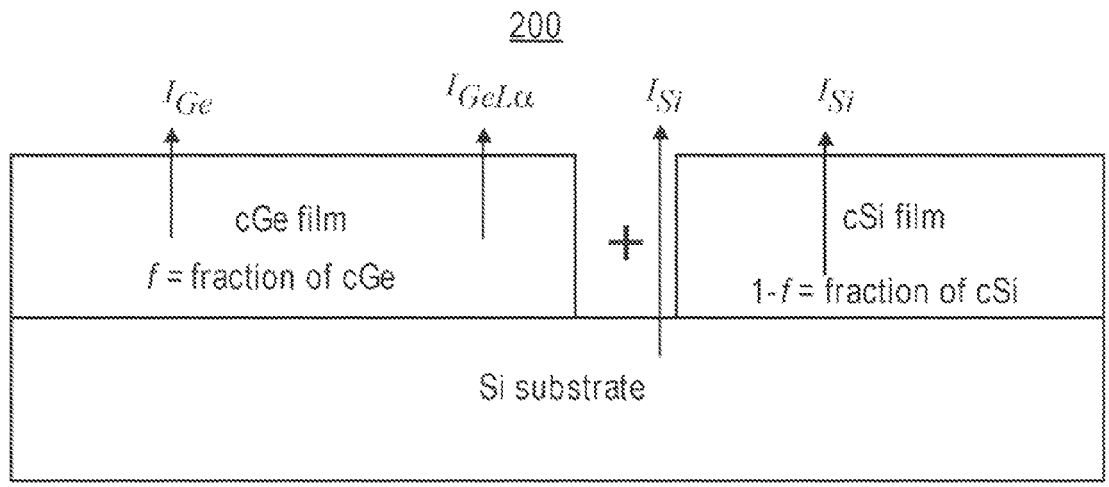
FIG. 2 illustrates a channel silicon germanium (cSiGe) film stack model, in accordance with an embodiment of the present invention.
FIG. 3A includes equations (1) through (3) that describe the intensity mixing model associated with the film stack model of FIG. 2, in accordance with an embodiment of the present invention.

As an example, FIG. 2 illustrates a channel silicon germanium (cSiGe) film stack model 200, in accordance with an embodiment of the present invention. Referring to FIG. 2, f represents the fraction of channel Ge (cGe) in a cSiGe film. The fraction of channel Si (cSi) in the cSiGe film is represented by 1-f. $I_{Ge}$ and $I_{Si}$ are the intensities measured by XPS, while $I_{GeL\alpha}$ is the measured XRF intensity.

FIG. 3A includes equations (1) through (3) that describe the intensity mixing model associated with the film stack model 200 of FIG. 2. Referring to equations (1), (2) and (3) of FIG. 3A, K is the corresponding material constant, and A is the corresponding attenuation term through the SiGe film that depends on the thickness (t) and the effective attenuation lengths (λ). In one embodiment, optimal values of both the SiGe thickness (t) and the Ge mixing fraction (f) that led to best agreement between the model and data are simultaneously determined via a non-linear regression analysis. FIG. 3B includes elaborated equations (1)-(3) of FIG. 3A that describe the relationships between each of the intensities and the thickness of the SiGe film. Referring to FIG. 3B, t, K and λ are corresponding film thickness, material constants and effective attenuation lengths.

Figure 4:
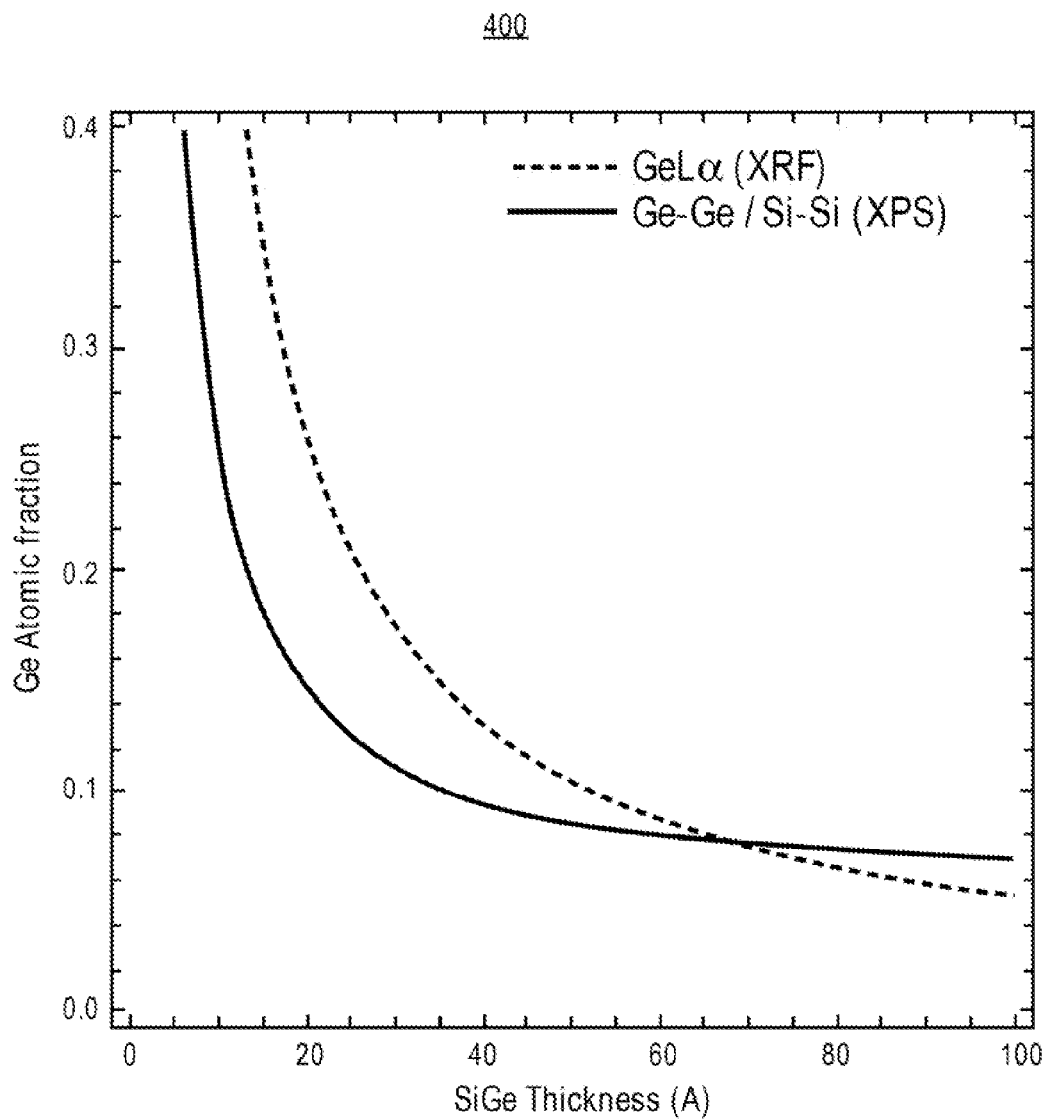
FIG. 4 is a plot showing the correlation between the Ge composition and the SiGe thickness for given XRF and XPS intensities as described by equations (1) through (3) of FIGS. 3A and 3B, in accordance with an embodiment of the present invention.

In an exemplary embodiment, for a thin SiGe layer which is less than 10 nanometers thick, photoelectrons from the substrate contribute to a measured Si2p XPS intensity. FIG. 4 is a plot 400 showing the correlation between the Ge composition and the SiGe thickness for given XRF and XPS intensities as described by equations (1) through (3) of FIGS. 3A and 3B. Plot 400 also graphically demonstrates how a unique solution can be found to determine Ge % and SiGe thickness, by using both the XPS and XRF signals. The dashed curve of plot 400 represents all the possible Ge % and SiGe thickness solutions for a given Ge fluorescence intensity.

Figure 5:
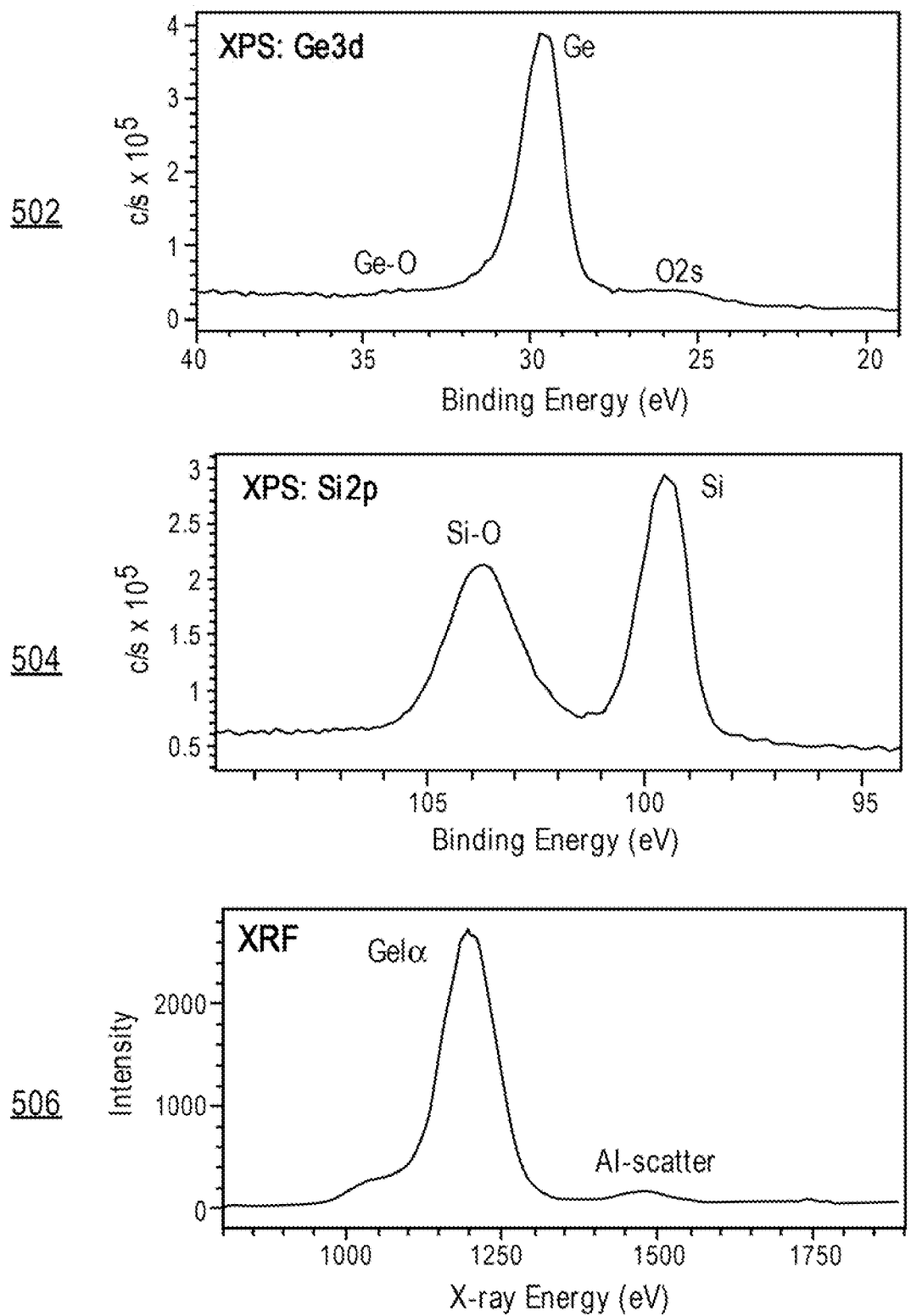
FIG. 5 includes plots showing examples of the XPS (Ge3d region), XPS (Si2p region) and the XRF (GeLα) spectra, as acquired simultaneously from a SiGe/Si sample, in accordance with an embodiment of the present invention.

FIG. 5 includes plots 502, 504, 506 showing examples of the XPS (Ge3d region), XPS (Si2p region) and the XRF (GeLα) spectra, respectively, as acquired simultaneously from a SiGe/Si sample, in accordance with an embodiment of the present invention. In addition to the Ge3d peak, the Ge3d region may exhibit peaks from Ge—O and O2s (plot 502). In the Si2p region, it is common that a Si—O peak is observed (plot 504), where the signal originates from native oxide at the surface. The GeLα XRF signal can be observed at around 1230 eV (plot 506). In one embodiment, the extraction of the XPS and XRF intensities is accomplished using well-established methods of background subtraction and Gaussian/Gauss-Lorentz peak fitting. For the case of XRF in particular, pure Gaussian multi-peak fitting typically leads to goodness of fit (GOF) fit-quality values of 0.97.

In another aspect, actual samples of SiGe on Si (or on thick SOI) were studied. In particular, 300 mm wafer samples of epitaxial SiGe from blanket wafers and patterned wafers were investigated. Both bare-Si(100) and SOI substrates were used. It is to be appreciated that, since XPS penetration depth is limited to approximately 10 nanometers, samples on thick SOI and bulk Si are similar from an XPS measurement perspective.

Figure 6:
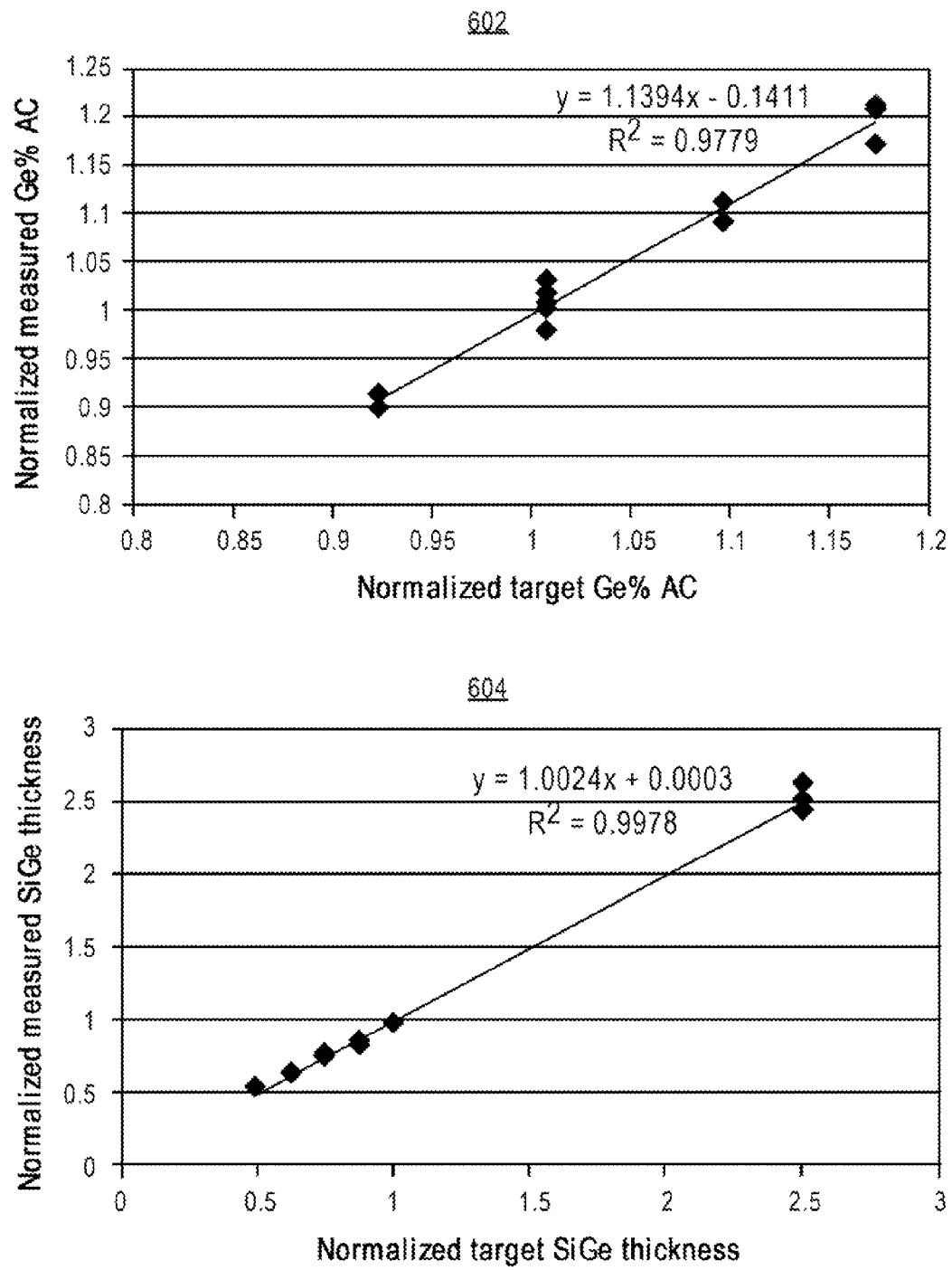
FIG. 6 includes normalized measured values plotted against the nominal SiGe composition and SiGe thicknesses, in accordance with an embodiment of the present invention.

In an embodiment, to evaluate the sensitivity of XPS-XRF measurements, a set of design of experiment (DOE) wafers was generated with various SiGe composition and thicknesses. The DOE consisted of 17 wafers with six different SiGe thickness splits over a wide range, and four composition splits with less than 5% atomic composition (AC) difference. The sensitivity of the XPS-XRF measurement on SiGe was investigated, along with its applicability over much thicker films, such as films greater than approximately 150 Angstroms. The validity of the film analysis model was also tested. Measurements were taken at both nine sites and 21 sites per wafer, but it was found that the results were very similar. FIG. 6 includes the normalized measured values plotted against the nominal composition (plot 602) and thicknesses (plot 604), in accordance with an embodiment of the present invention.

Referring to FIG. 6, plots of normalized measured Ge % AC (plot 602) and SiGe thickness (plot 604) versus the targeted values are provided. The plots show an excellent correlation between the measured and targeted values, with a slope close to 1.0, and $R^2 > 0.97$. Accordingly, the measurements are highly sensitive to process change. Additionally, data indicate that the composition and thickness measurements are decoupled. The results also indicate that the film stack model using both XPS and XRF signals, represented by FIG. 2 and Equations (1) through (3) of FIGS. 3A and 3B, represents the SiGe/Si system very well.

Figure 7:
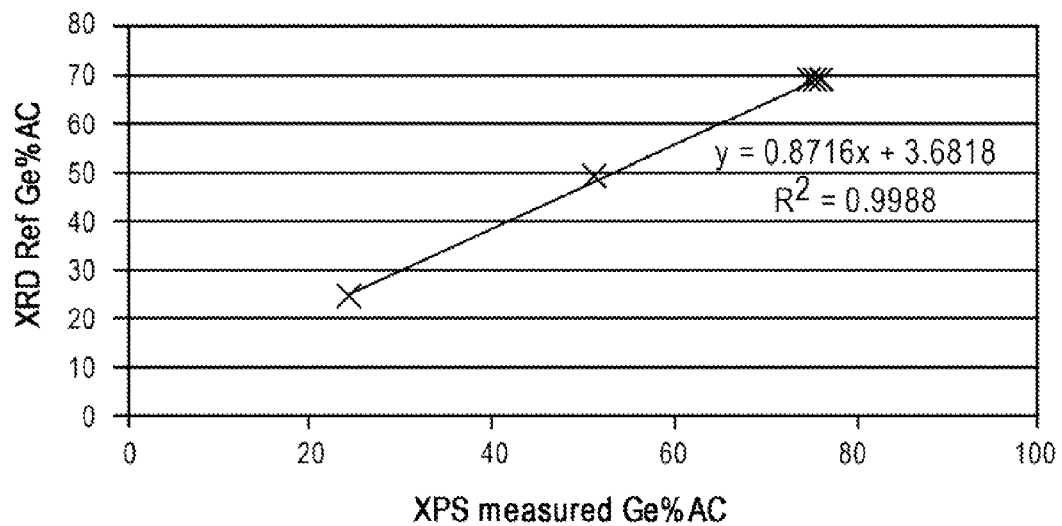
FIG. 7 includes plots showing good linearity between XPS measured SiGe atomic composition and SiGe thickness to an XRD reference, in accordance with an embodiment of the present invention.
Figure 7:
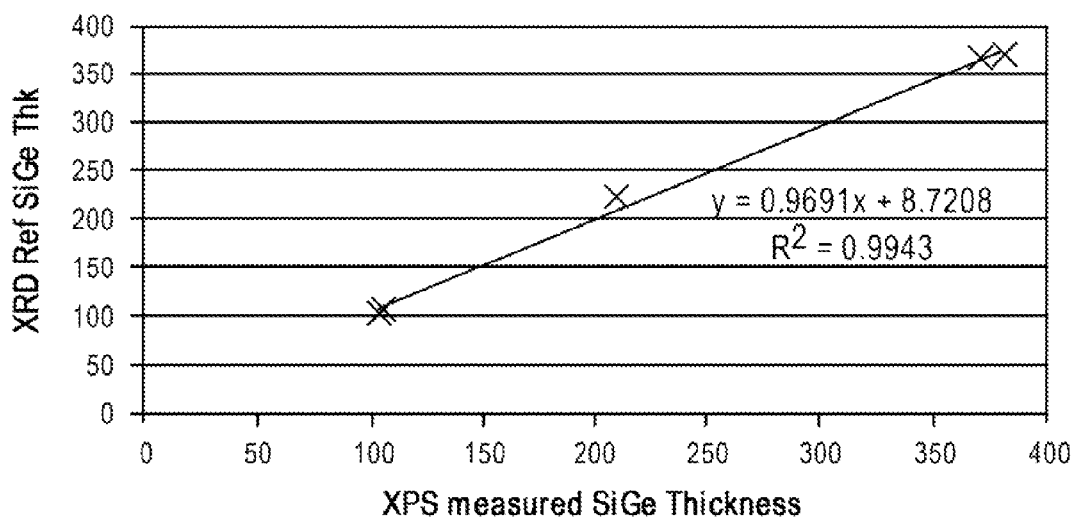

A separate set of samples with various Ge % AC and SiGe thickness on blanket wafers was used to evaluate the accuracy of the XPS-XRF measurement, by comparing the samples to a high resolution x-ray diffraction (HR-XRD) reference metrology. A wide composition range was used in the set of wafer samples, from 25% to 75% of total Ge content. Since HR-XRD measurements are more reliable with thicker films, the thickness ranged from about 100 Angstroms to about 400 Angstroms. FIG. 7 includes plots showing good linearity between XPS measured SiGe atomic composition (plot 702) and SiGe thickness (plot 704) to an XRD reference, in accordance with an embodiment of the present invention.

Referring to FIG. 7, the two measurements correlate very well and are highly linear over a wide range of thickness and composition. From the measurement of such thicker SiGe films, which are traditionally too thick for XPS measurement, in accordance with one or more embodiments described herein, it is shown that simultaneous XRF-XPS metrology can extend traditional XPS capabilities. In one such embodiment, however, extending the capabilities involves the assumption that the SiGe composition remains constant over the entire film.

In another aspect, as a variation of SiGe applications, structures involving a SiGe layer integrated with an ultra-thin body and buried oxide (UTBB) for fully depleted silicon on insulator (FDSOI) devices were investigated. A pFET channel of such a device may be compressively strained with SiGe. In accordance with an embodiment of the present invention, Ge enrichment can be used to generate SiGe on insulator samples and achieve a thin compressive strained layer. Ge enrichment is initiated with a thin oxide layer deposited to stabilize the surface of the SiGe layer, followed by a standard rapid thermal oxidation (RTO) process to oxidize the SiGe and push the Ge atoms in the underlying SOI, yielding approximately 7 nm SGOI containing a range of approximately 15-35% Ge.

In an embodiment, a UTBB SiGe application can be used in the precision evaluation of the combined XPS-XRF metrology tool. In an example, both static and dynamic precision were evaluated with UTBB FDSOI product wafers. The measurements were performed on 50 $\mu m^2$ metrology boxes to evaluate factors such as x-ray beam size consistency and spillage that might affect the precision of product wafer measurement in high volume production.

Figure 8A:
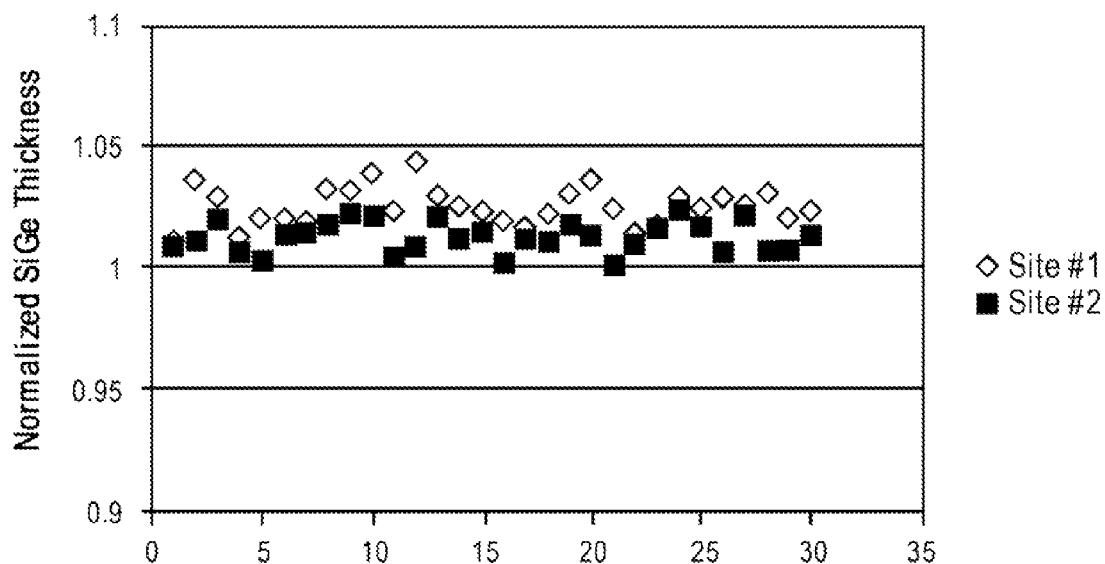
FIG. 8A includes plots of SiGe thickness and Ge % from a static precision measurement, in accordance with an embodiment of the present invention.
Figure 8A:
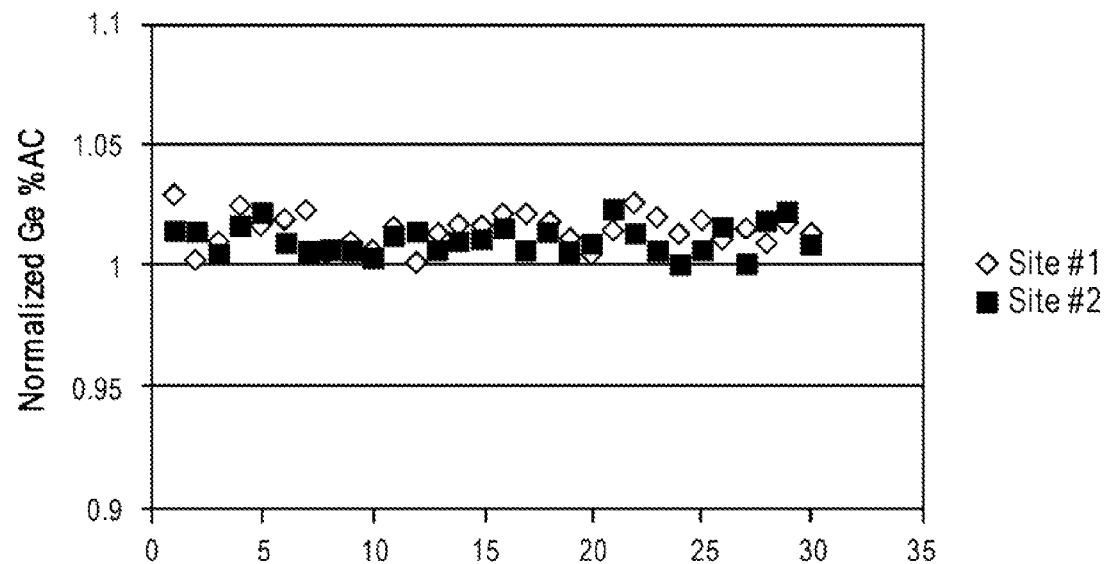
Figure 8B:
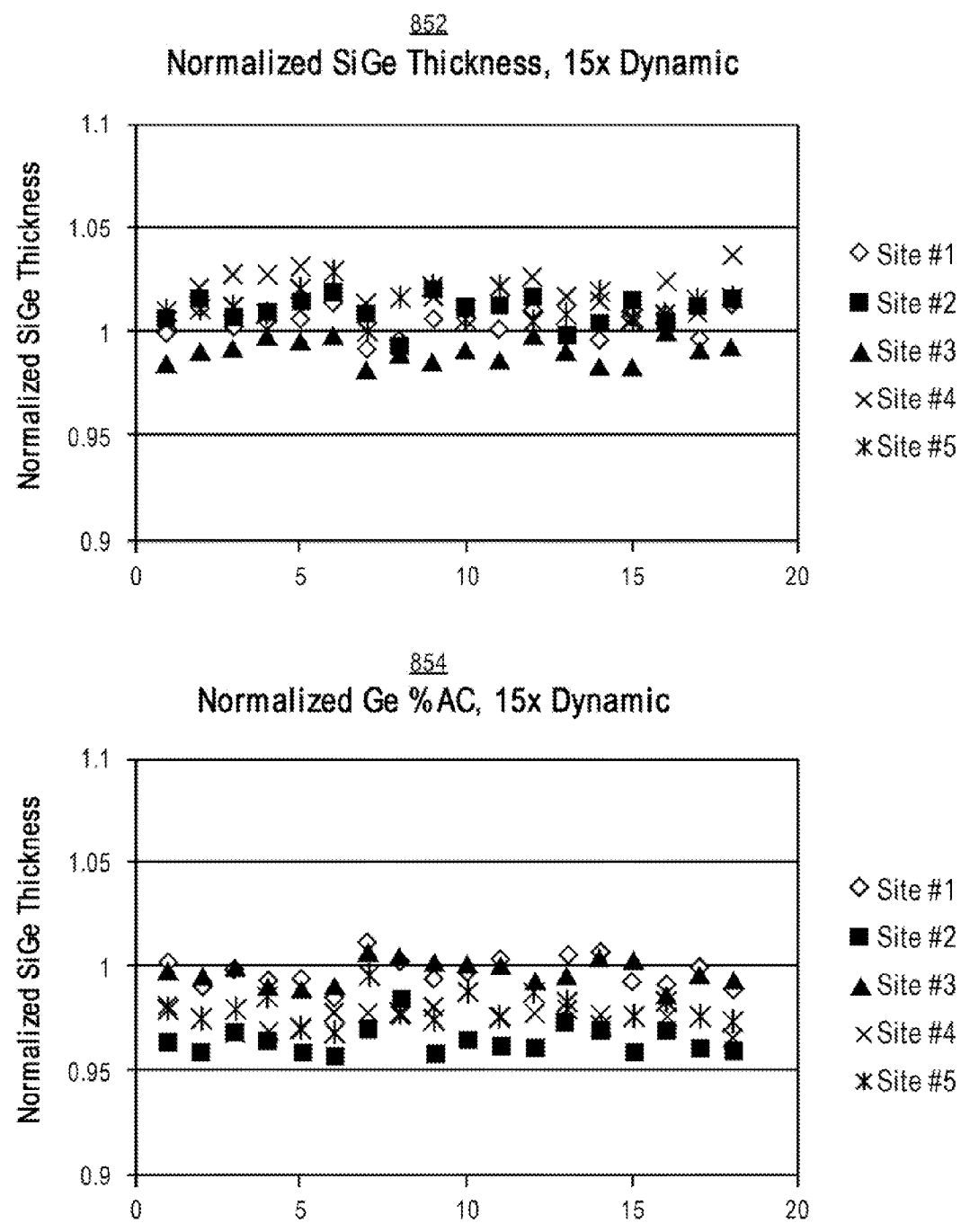
FIG. 8B includes plots of SiGe thickness and Ge % from a dynamic precision measurement, in accordance with an embodiment of the present invention.

Static precision, also known as measurement repeatability, was collected by measuring the same site for 30 times, averaging over two sites. Dynamic precision, also known as measurement reproducibility, were evaluated by measuring five sites per wafer, repeating the measurement by wafer loading/unloading for a total of 18 times. In analyzing the dynamic precision data, the standard deviation of each measurement site was first determined separately, and then the relative standard deviation (RSD) of the five sites were averaged. Accordingly, the precision is reported in terms of RSD of the mean value. FIG. 8A includes plots of SiGe thickness (plot 802) and Ge % (plot 804) from a static precision measurement. FIG. 8B includes plots of SiGe thickness (plot 852) and Ge % (plot 854) from a dynamic precision measurement.

Referring to FIGS. 8A and 8B, precision evaluation of SiGe thickness and Ge % AC from XPS+XRF measurements is provided. The plots involve normalized measurements of SiGe thickness and Ge % atomic composition. The RSD of measurements of less than 1% indicate a very stable, reproducible and production worthy metrology tool. The RSD numbers are also listed in Table 900 of FIG. 9.

Figure 10:
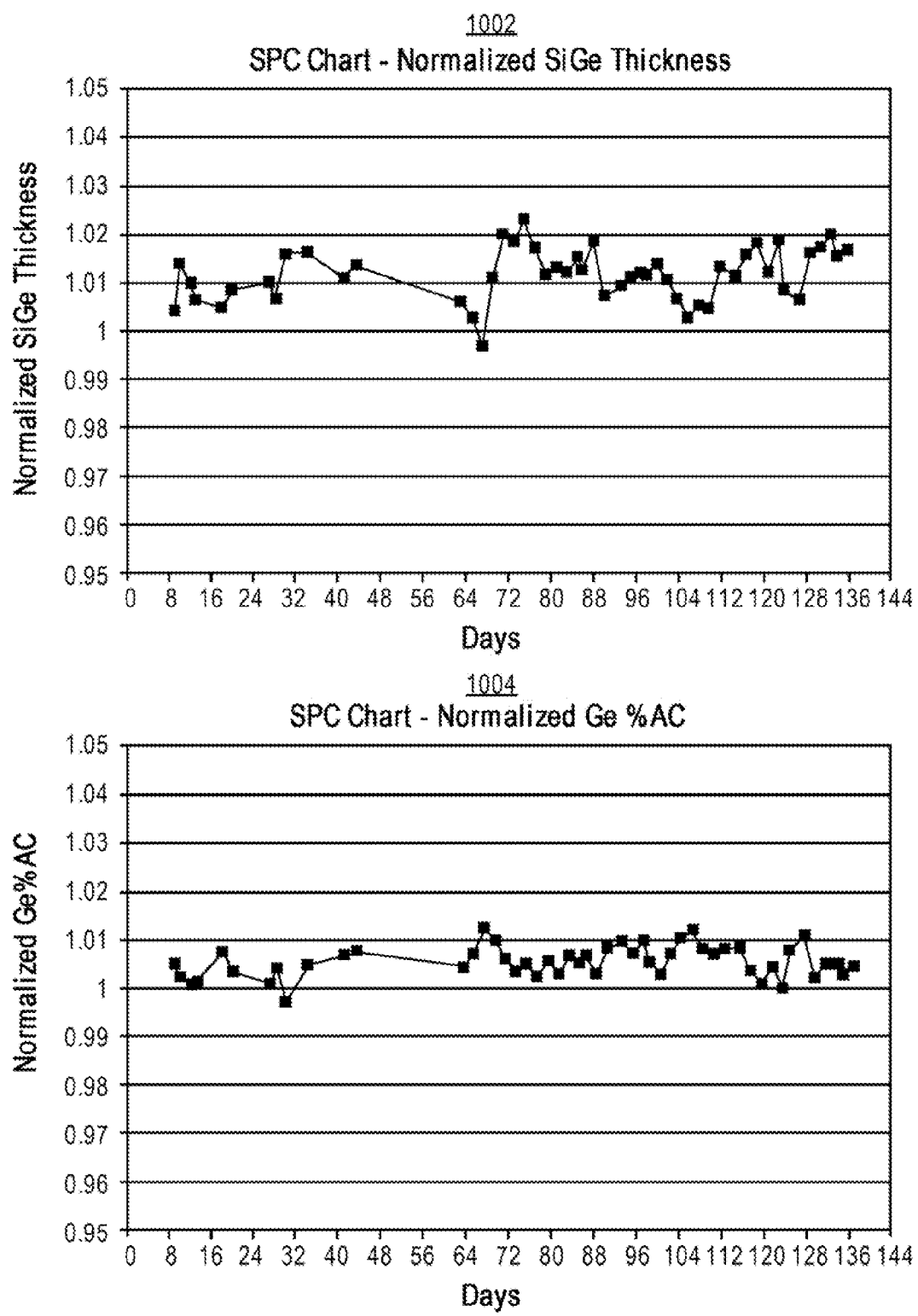
FIG. 10 shows statistical process control (SPC) data charted over a 4-month period for SiGe thickness and for normalized Ge % AC, in accordance with an embodiment of the present invention.

In accordance with an embodiment of the present invention, to further determine the production worthiness of a combined XPS-XRF metrology tool such as the tool described in association with FIG. 1, long-term stability was evaluated by collecting statistical process control (SPC) data from the tool over an extended period of time. A control SiGe wafer was used for this purpose. The control SiGe wafer was capped with an approximately 13 Angstrom hafnium oxide ($HfO_2$) film to minimize the formation of either $SiO_2$ or $GeO_2$, which might otherwise change the SiGe composition and thickness over time. The same control wafer was measured about 3-4 times per week with the assistance of fab automation. FIG. 10 shows statistical process control (SPC) data charted over a 4-month period for SiGe thickness (plot 1002) and for normalized Ge % AC (plot 1004), in accordance with an embodiment of the present invention.

Referring to FIG. 10, the normalized wafer average of SiGe thickness and Ge % AC over a period of 4 months shows that the measurements are very stable, with SiGe thickness RSD at approximately 0.53%, and Ge % AC RSD at approximately 0.33%. The values are also tabulated in Table 900 of FIG. 9. Thus, in an embodiment, with the combination of XPS with XRF measurements, metrology for SiGe related process technology in a high volume manufacturing environment can be achieved with ease, while maintaining the sensitivity, precision and stability of the measurements.

Summarizing the above evaluations, in accordance with an embodiment of the present invention, silicon germanium composition and thickness determination can be made via simultaneous small-spot XPS and XRF Measurements. The thickness and composition determination of SiGe films may be made using simultaneous XPS and XRF measurements. Measurements of SiGe films in various applications have been explored, as described above. The measurements are sensitive and linear over a much wider range of SiGe thickness, with excellent precision. Long term stability of the measurement is also shown to be very good.

Embodiments of the present invention may be provided as a computer program product, or software, that may include a machine-readable medium having stored thereon instructions, which may be used to program a computer system (or other electronic devices) to perform a process according to an embodiment of the present invention. In one embodiment, the computer system is coupled with the XPS+XRF combination tool described in association with FIG. 1. A machine-readable medium includes any mechanism for storing or transmitting information in a form readable by a machine (e.g., a computer). For example, a machine-readable (e.g., computer-readable) medium includes a machine (e.g., a computer) readable storage medium (e.g., read only memory ("ROM"), random access memory ("RAM"), magnetic disk storage media, optical storage media, flash memory devices, etc.), a machine (e.g., computer) readable transmission medium (electrical, optical, acoustical or other form of propagated signals (e.g., infrared signals, digital signals, etc.)), etc.

Figure 11:
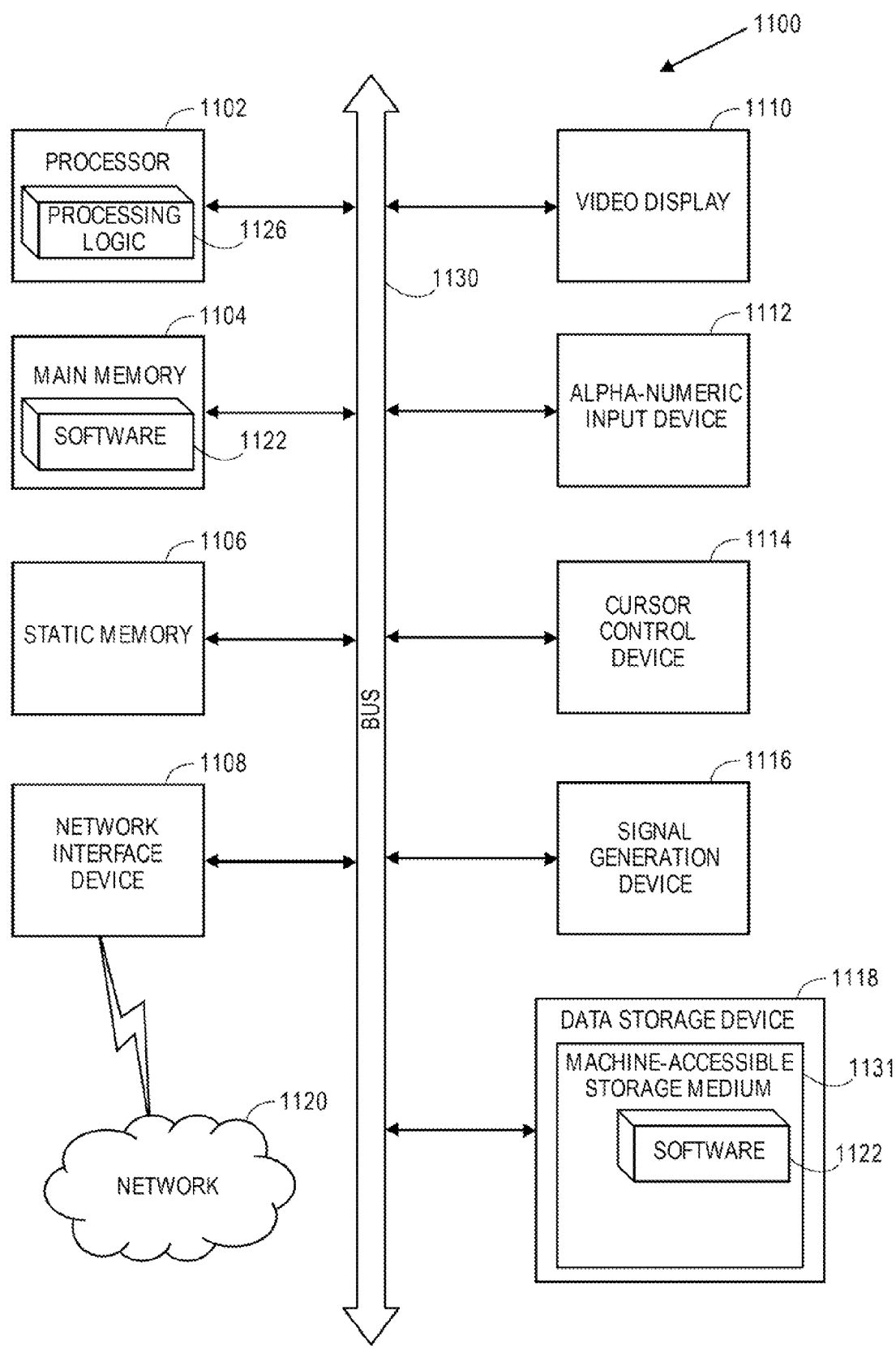
FIG. 11 illustrates a block diagram of an exemplary computer system, in accordance with an embodiment of the present invention.

FIG. 11 illustrates a diagrammatic representation of a machine in the exemplary form of a computer system 1100 within which a set of instructions, for causing the machine to perform any one or more of the methodologies discussed herein, may be executed. In alternative embodiments, the machine may be connected (e.g., networked) to other machines in a Local Area Network (LAN), an intranet, an extranet, or the Internet. The machine may operate in the capacity of a server or a client machine in a client-server network environment, or as a peer machine in a peer-to-peer (or distributed) network environment. The machine may be a personal computer (PC), a tablet PC, a set-top box (STB), a Personal Digital Assistant (PDA), a cellular telephone, a web appliance, a server, a network router, switch or bridge, or any machine capable of executing a set of instructions (sequential or otherwise) that specify actions to be taken by that machine. Further, while only a single machine is illustrated, the term "machine" shall also be taken to include any collection of machines (e.g., computers) that individually or jointly execute a set (or multiple sets) of instructions to perform any one or more of the methodologies discussed herein. For example, in an embodiment, a machine is configured to execute one or more sets of instruction for calibrating an XPS signal measurement with an XRF signal measurement.

The exemplary computer system 1100 includes a processor 1102, a main memory 1104 (e.g., read-only memory (ROM), flash memory, dynamic random access memory (DRAM) such as synchronous DRAM (SDRAM) or Rambus DRAM (RDRAM), etc.), a static memory 1106 (e.g., flash memory, static random access memory (SRAM), etc.), and a secondary memory 1118 (e.g., a data storage device), which communicate with each other via a bus 1130.

Processor 1102 represents one or more general-purpose processing devices such as a microprocessor, central processing unit, or the like. More particularly, the processor 1102 may be a complex instruction set computing (CISC) microprocessor, reduced instruction set computing (RISC) microprocessor, very long instruction word (VLIW) microprocessor, processor implementing other instruction sets, or processors implementing a combination of instruction sets. Processor 1102 may also be one or more special-purpose processing devices such as an application specific integrated circuit (ASIC), a field programmable gate array (FPGA), a digital signal processor (DSP), network processor, or the like. Processor 1102 is configured to execute the processing logic 1126 for performing the operations discussed herein.

The computer system 1100 may further include a network interface device 1108. The computer system 1100 also may include a video display unit 1110 (e.g., a liquid crystal display (LCD) or a cathode ray tube (CRT)), an alphanumeric input device 1112 (e.g., a keyboard), a cursor control device 1114 (e.g., a mouse), and a signal generation device 1116 (e.g., a speaker).

The secondary memory 1118 may include a machine-accessible storage medium (or more specifically a computer-readable storage medium) 1131 on which is stored one or more sets of instructions (e.g., software 1122) embodying any one or more of the methodologies or functions described herein. The software 1122 may also reside, completely or at least partially, within the main memory 1104 and/or within the processor 1102 during execution thereof by the computer system 1100, the main memory 1104 and the processor 1102 also constituting machine-readable storage media. The software 1122 may further be transmitted or received over a network 1120 via the network interface device 1108.

While the machine-accessible storage medium 1131 is shown in an exemplary embodiment to be a single medium, the term "machine-readable storage medium" should be taken to include a single medium or multiple media (e.g., a centralized or distributed database, and/or associated caches and servers) that store the one or more sets of instructions. The term "machine-readable storage medium" shall also be taken to include any medium that is capable of storing or encoding a set of instructions for execution by the machine and that cause the machine to perform any one or more of the methodologies of the present invention. The term "machine-readable storage medium" shall accordingly be taken to include, but not be limited to, solid-state memories, and optical and magnetic media.

Thus, systems and approaches for silicon germanium thickness and composition determination using combined XPS and XRF technologies have been disclosed.

What is claimed is:

1. A method for characterizing a silicon germanium film, said method comprising:
   generating an X-ray beam;
   positioning a sample in a pathway of said X-ray beam;
   collecting an X-ray photoelectron spectroscopy (XPS) signal generated by bombarding said sample with said X-ray beam;
   collecting an X-ray fluorescence (XRF) signal generated by bombarding said sample with said X-ray beam;
   determining a thickness of the silicon germanium film from the XRF signal and the XPS signal; and
   determining a composition of the silicon germanium film from the XRF signal and the XPS signal, wherein determining the composition of the silicon germanium film comprises comparing the XRF signal and the XPS signal to a realistic material layer mixing model that scales the predicted intensity of an XPS Ge signal and an XRF Ge signal relative to a pure germanium film, constraining the remaining fraction of the silicon germanium film to Si.

2. The method of claim 1, wherein collecting the XPS signal and collecting the XRF signal is performed simultaneously.

3. The method of claim 1, wherein collecting the XPS signal and collecting the XRF signal comprises collecting within an approximately 50 $\mu m^2$ metrology box of the sample.

4. The method of claim 1, wherein determining the thickness of the silicon germanium film comprises determining the thickness of a silicon germanium channel layer of a semiconductor device.

5. The method of claim 1, wherein determining the thickness of the silicon germanium film comprises determining the thickness of a silicon germanium source or drain region of a semiconductor device.

6. A method for characterizing a silicon germanium film, said method comprising:
   generating an X-ray beam;
   positioning a sample in a pathway of said X-ray beam;
   collecting an X-ray photoelectron spectroscopy (XPS) signal generated by bombarding said sample with said X-ray beam;
   collecting an X-ray fluorescence (XRF) signal generated by bombarding said sample with said X-ray beam; and
   determining a composition of the silicon germanium film from the XRF signal and the XPS signal, wherein determining the composition of the silicon germanium film comprises comparing the XRF signal and the XPS signal to a realistic material layer mixing model that scales the predicted intensity of an XPS Ge signal and an XRF Ge signal relative to a pure germanium film, constraining the remaining fraction of the silicon germanium film to Si.

7. The method of claim 6, wherein collecting the XPS signal and collecting the XRF signal is performed simultaneously.

8. The method of claim 6, wherein collecting the XPS signal and collecting the XRF signal comprises collecting within an approximately 50 $\mu m^2$ metrology box of the sample.

9. The method of claim 6, wherein determining the composition of the silicon germanium film comprises determining the composition of a silicon germanium channel layer of a semiconductor device.

10. The method of claim 6, wherein determining the composition of the silicon germanium film comprises determining the composition of a silicon germanium source or drain region of a semiconductor device.

* * * * *